United States Patent [19]

Niezink et al.

[11] Patent Number: 5,370,611
[45] Date of Patent: Dec. 6, 1994

[54] INJECTOR

[75] Inventors: Herman Niezink, Wierden; Franciscus H. C. Benning, Almelo, both of Netherlands

[73] Assignee: Texas Instruments Incorporated, Dallas, Tex.

[21] Appl. No.: 136,490

[22] Filed: Oct. 13, 1993

Related U.S. Application Data

[63] Continuation of Ser. No. 910,207, Jul. 8, 1992, abandoned.

[30] Foreign Application Priority Data

Jul. 8, 1991 [NL] Netherlands ................ 9101197

[51] Int. Cl.⁵ ............................................. A61M 36/04
[52] U.S. Cl. ................................... 604/62; 604/57; 604/59
[58] Field of Search ............... 604/57, 59–64, 604/158, 218; 606/116, 117

[56] References Cited

U.S. PATENT DOCUMENTS

| | | | |
|---|---|---|---|
| 2,130,305 | 9/1938 | Lewis | 604/59 |
| 3,675,639 | 7/1972 | Cimber | 604/60 |
| 4,341,211 | 7/1982 | Kline | 604/60 |
| 4,834,704 | 5/1989 | Reinicke | 604/57 |
| 4,950,234 | 8/1990 | Fujioka et al. | 604/60 |
| 5,135,493 | 8/1992 | Peschke | 604/59 |
| 5,211,129 | 5/1993 | Taylor et al. | 606/117 |
| 5,288,291 | 2/1994 | Teoh | 604/59 |

FOREIGN PATENT DOCUMENTS 8901858  2/1991  Netherlands .................. 604/61

*Primary Examiner*—Ralph A. Lewis
*Attorney, Agent, or Firm*—Rebecca A. Mapstone; James C. Kesterson; Richard L. Donaldson

[57] ABSTRACT

Injector (1), comprising a housing to which is fixed a hollow needle (17) provided with conveyance means (3,4) for moving an object such as a transponder (22) through said needle (17). Such transponders (22) are inserted in living beings for identification purposes. Metering means (11,12) are provided in the injector (1)in order to permit the introduction of a fluid such as a disinfectant during the insertion of such objects (22). Such means comprise a storage place for fluid (11) which is connected to channel means (8) which open into the movement path of the object (22). In this way fluid is added during the positioning of the object (22).

5 Claims, 2 Drawing Sheets

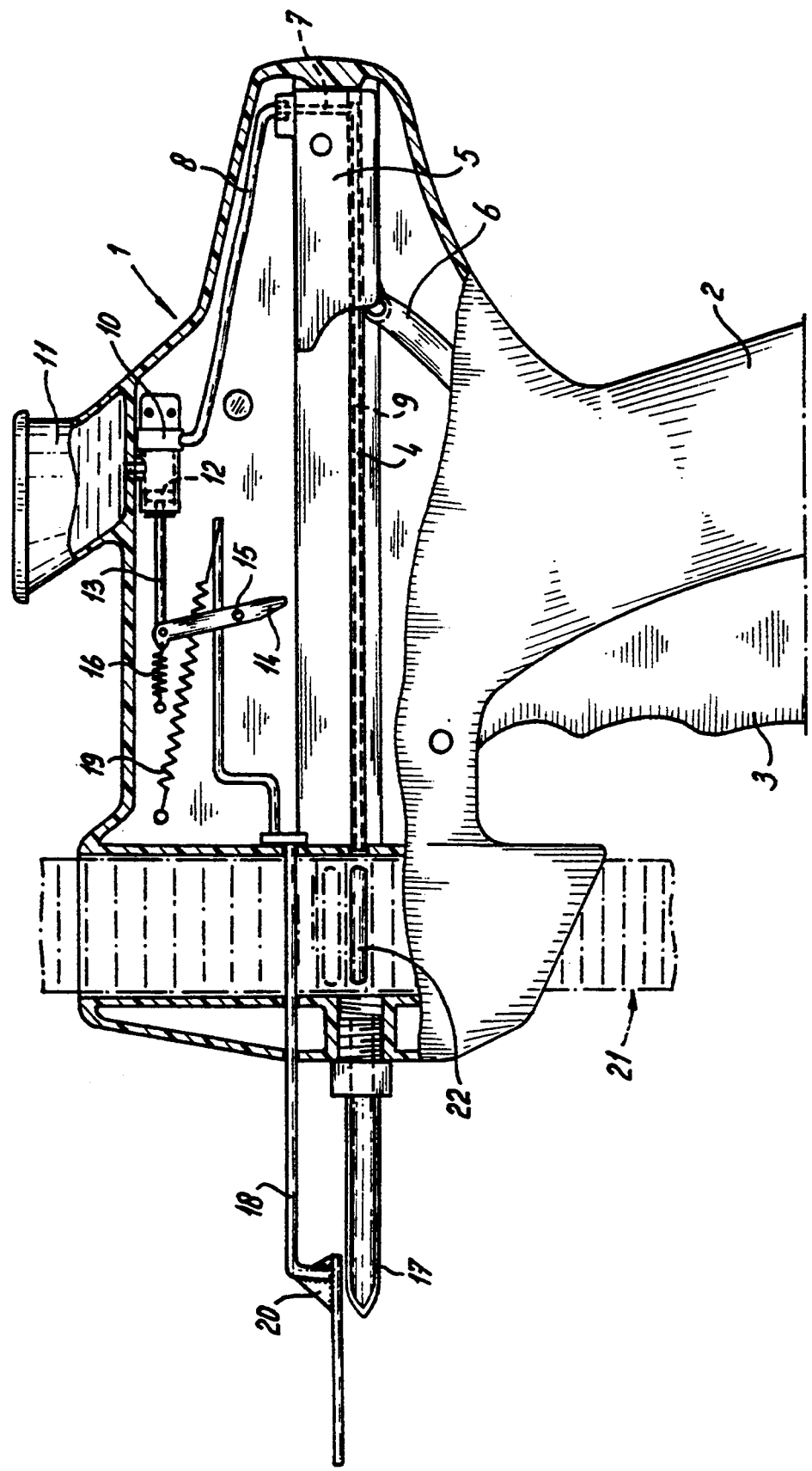

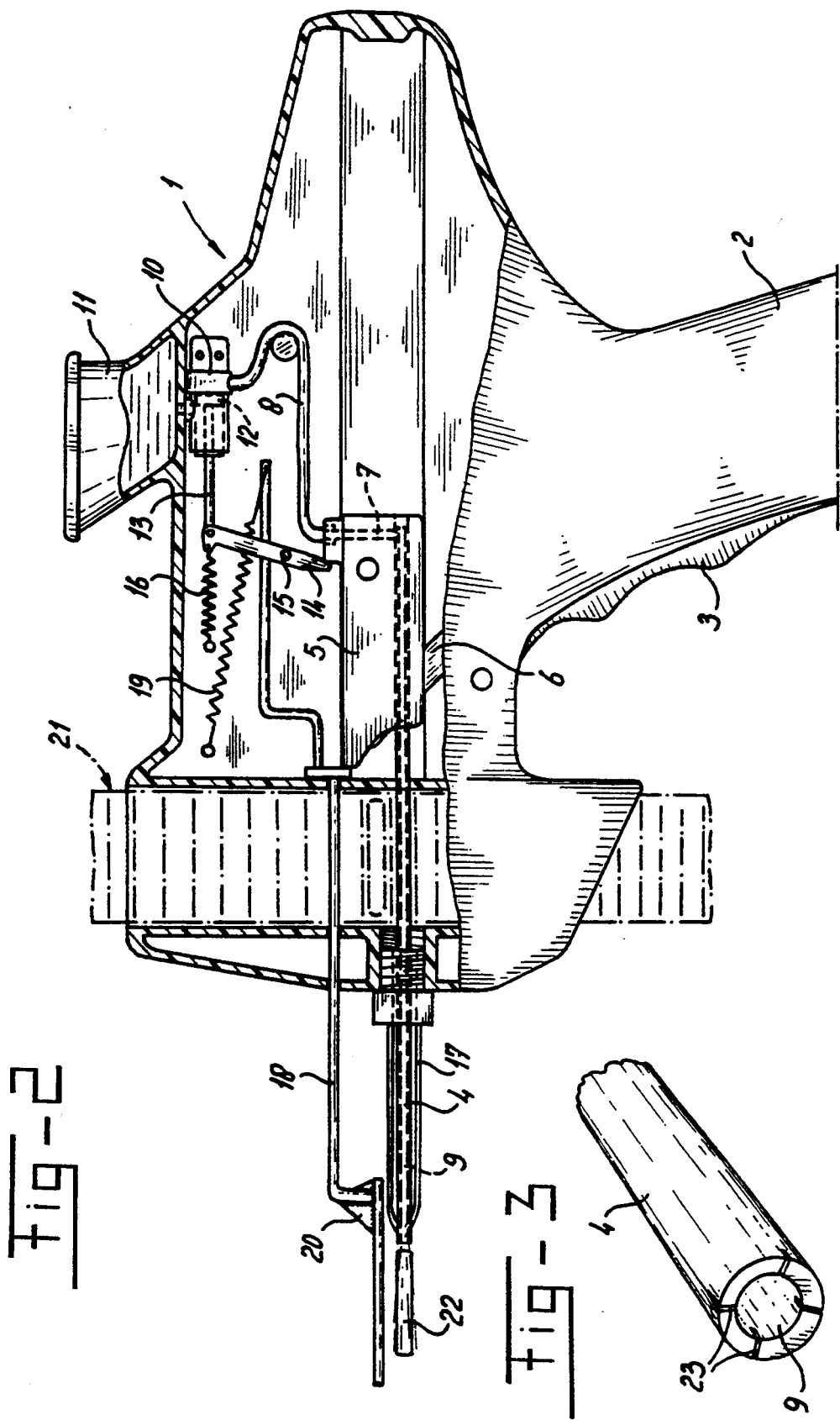

INJECTOR

This application is a continuation of application Ser. No. 07/910,207 filed Jul. 8, 1992 now abandoned.

FIELD OF THE INVENTION

The present invention relates to an injector, comprising a housing, with a hollow needle fixed thereto and provided with conveyance means for moving an object such as a transponder through said needle.

BACKGROUND OF THE INVENTION

Such an injector is generally known in the art and is used for, for example, introducing identification means such as transponders into living beings such as pigs. Such transponders can be accommodated in a cartridge, which cartridge is fitted in an injector, and the transponders are moved by means of a push rod out of the cartridge into the hollow needle. With said hollow needle an incision is first made in the skin and the underlying tissue of the animal is exposed, and the transponder is then moved into its end position with the aid of the push rod. The needle is then withdrawn.

Although various proposals have been made for limiting as much as possible the introduction of impurities into the incision in the living being, such as making a U-shaped incision in the skin, the risk of infection still remains. The risk associated with infection is that the transponder will be expelled from the body of the animal through the body's defence mechanisms.

It was therefore proposed in the art that disinfectants should be used during the insertion of the transponder. Such disinfectants can be moved together with the transponder into the living being in question. One possibility is to confine the transponder in a cartridge with an ointment-like material having disinfectant properties. When the transponder is ejected from the cartridge, said ointment will also be conveyed. It was, however, found in experiments that only a limited part of the ointment present in the space of the transponder goes into the skin at the incision. In experiments less than a few per cent was found in the wound itself. The major part of the ointment remains behind in the injector. It was also found that a considerable variation existed in the quantity of disinfectant introduced into the wound. The certainty of the transponders remaining in the body is therefore reduced, and subsequent checking is necessary. Efforts toward the general use of transponders in livestock are thus impeded.

This means that the injector must be made in such a way that it is always ensured that an adequate quantity of disinfectant is introduced into the wound. On the other hand, too much disinfectant must not be introduced into the wound, because this can slow down the encapsulation of the transponder inside the animal, or can have other negative effects.

SUMMARY OF THE INVENTION

The object of the present invention is to provide an injector of the above-mentioned type, with which it is possible for the handler in a controlled manner to administer a disinfecting fluid into the wound in controlled quantities, without the carrying out of special measures.

This object is achieved with an injector of the type described above in that the injector contains metering means comprising a fluid storage connected with channel means opening in the path of movement of the object.

The invention is based on the idea that the fluid, which may have disinfecting properties, but can also have other desired properties associated with the insertion of a transponder into a living being, should not be inserted into the path of movement of the transponder, but conveyed separately therefrom through the channel means, i.e. that the space around the transponder in the cartridge no longer determines the quantity of fluid which can be conveyed.

According to an advantageous embodiment of the invention, the channel means are embodied for releasing a fluid near the position where the object is inserted. In this embodiment, movement of the fluid takes place separately from movement of the transponder. Only when the transponder is released from the hollow needle to the living being in question the fluid in question is supplied to it.

The channel means can be provided in all parts of the injector situated near the insertion point of the transponder, i.e. in either the needle or the conveyance means. Since the conveyance means in general have the greatest surface area for containing a bore, and since it is relatively simple to connect a fluid storage supply thereto, the channel means are preferably fitted in the conveyance means.

In order to facilitate release of the fluid at the end of the conveyance means, the face which engages the object such as the transponder is provided with recesses in order to permit movement of fluid between said face and the object in question.

The conveyance means preferably comprise a push rod which is known per se in the art, and the length of the hollow needle and the rod is such that in the end position of the push rod it projects past the needle.

The metering means preferably also have control means for the release of fluid at the correct moment. This release preferably takes place at the end of the movement of the conveyance means.

BRIEF DESCRIPTION OF THE DRAWINGS

The invention will be explained in greater detail below with reference to an example of an embodiment shown in the drawings, in which:

FIG. 1 shows in side view partially in section a preferred embodiment of an injector according to the invention in a first rest position;

FIG. 2 shows the injector according to FIG. 1 in an end position at the moment of placing of a transponder in a living being; and FIG. 3 shows a perspective detail of the front end of the push rod used in the injector according to FIGS. 1 and 2.

DESCRIPTION OF THE PREFERRED EMBODIMENTS

In FIG. 1 an injector according to the invention is shown in its entirety by 1. It comprises a housing 2, provided with a trigger 3 for operating both a push rod 4 and a block 5 by means of a lever 6. Block 5 is provided with a nesting place for push bar 4 and is provided with a passage 7, to which at one side a pipe 8 connects and at the other side of which a bore 9 is provided in the push rod 4. Pipe 8 is connected at the other side to the outlet of a piston/cylinder unit 10 with a storage 11 for fluid. Piston 12 of piston/cylinder unit 10 is provided with a control rod 13 to which a lever 14 is connected, which lever can rotate about a hinge point 15 fixed to housing 2. Control rod 13 in FIG. 1 is driven to the left by means of a spring 16.

Injector 1 is provided with a hollow needle 17, which at one side is open in order in that way to obtain a U-shaped incision in the skin (opening flap) when said needle is inserted into the body. A positioning element 18 which is laid against the outside of the animal in question is also present. Such a positioning element is preferably used for the injection of transponders into pigs, the positioning element being placed in the space bounded between the ear and the head. The positioning element 18 is slidable relative to injector 2 and is held in the outward driven position by means of spring 19. Positioning element 18 is provided with a stop 20 which acts on the animal.

A cartridge within which transponders 22 are situated is indicated by 21.

The way in which positioning element 18 functions as such is not important for the present invention. A part of the functioning thereof will be explained briefly with reference to FIGS. 1 and 2. On insertion of the needle 17, positioning element 18 will be moved to the right out of the position shown in FIG. 1 through resting of stop 20 against the head of the animal. Through operation of the trigger 3, push rod 4 will be moved to the left, and will release a transponder 22 from cartridge 21 and convey it to the left through needle 17. Block 5 will also move to the left in FIG. 1 to the position shown in FIG. 2. On this movement to the left block 5 strikes against lever 14 and also presses positioning element 18 out of the position (not shown) in which it is moved to the right back to the position on the left, as shown in FIG. 2. With this last action needle 17 together with injector 1 is moved outwards because stop 20 and positioning element 18 in general remain in the same position relative to the animal. Through the knocking of block 5 against lever 14, piston 12 is operated, as a result of which an accurately determined quantity of fluid is moved from storage 11 via pipe 8 and channel 7 through bore 9 of the push rod 4. This fluid comes out at the end of push rod 4 behind the transponder, as illustrated in FIG. 2.

It can be seen from the arrangement of the various parts that fluid is added only at the end of the stroke of the push rod, i.e. at a moment when transponder 22 is situated near the end of the hollow needle 17. Only at that moment is it necessary to feed fluid, which can have, for example, a disinfecting action, to the living being. Unnecessary waste is thus avoided, and it is ensured that the correct quantity of fluid is applied at the correct time.

In order to facilitate the outflow of fluid at the contact face between the end of push rod 4 and the rear side of the transponder 21, the end of the push rod is preferably designed as shown in the embodiment of FIG. 3. In this embodiment recesses or grooves 23 which are connected to aperture 9 are provided, through which fluid can move out between the push rod 4 and the transponder into the opening in the body provided for it.

Although the invention is described above with reference to a preferred embodiment, it must be understood that numerous modifications can be made to it without going beyond the scope of the present application. For example, numerous embodiments are conceivable with regard to the metering of fluid in bore 9 of push rod 4. All that is important is that fluid should be added in a controlled manner only at the end of the outward movement of the transponder. It is also possible to make the supply of fluid take place through a separate bore in the hollow needle 16. The end of such a bore preferably lies at the end of the needle, but this is not always necessary. It has been described above that the release of fluid takes place at the end of the movement of the push rod. It is, however, also possible to introduce fluid at another time, such as at the beginning of the movement of the push rod.

We claim:

1. An injector for inserting objects at selected positions comprising:
   a housing;
   a hollow needle attached to said housing;
   conveyance means provided within said housing for moving an object by contact along a path through said needle; and
   metering means provided within said housing, said metering means comprising a fluid storage area for storing a selected amount of fluid and a channel means connected between the fluid storage area and said path, said channel means releasing fluid from said fluid storage area to said path subsequent to and in response to said conveyance means moving said object along said path through said needle.

2. An injector according to claim 1, wherein said channel means also releases said fluid near the inserted position of said object.

3. Injector according to claim 1, in which the conveyance means comprise a push rod, having length and two ends, and a hole bored through it along it's length, through which said fluid, as it is released from said channel means, enters into one end of said push-rod, travels through the push-rod and exits out the other end of said push-rod.

4. Injector according to claim 3, wherein said other end of said push-rod has a face which is provided with recesses through which said fluid as it is released from said channel means and travels into one end of and through said push-rod, exits out.

5. Injector according to claim 3, wherein the length of the hollow needle and rod is such that in the end position, the push rod projects through and beyond the needle.

* * * * *